(12) United States Patent
Griffey et al.

(10) Patent No.: US 9,713,550 B2
(45) Date of Patent: *Jul. 25, 2017

(54) REDUCED-PRESSURE, COMPOSITE MANIFOLDS

(71) Applicant: KCI LICENSING, INC., San Antonio, TX (US)

(72) Inventors: Edward S. Griffey, Fair Oaks Ranch, TX (US); Larry Tab Randolph, San Antonio, TX (US); Charles Alan Seegert, North Richland Hills, TX (US)

(73) Assignee: KCI Licensing, Inc., San Antonio, TX (US)

( * ) Notice: Subject to any disclaimer, the term of this patent is extended or adjusted under 35 U.S.C. 154(b) by 25 days.

This patent is subject to a terminal disclaimer.

(21) Appl. No.: 14/320,234

(22) Filed: Jun. 30, 2014

(65) Prior Publication Data

US 2014/0336603 A1 Nov. 13, 2014

Related U.S. Application Data

(63) Continuation of application No. 12/620,086, filed on Nov. 17, 2009, now Pat. No. 8,802,916.

(Continued)

(51) Int. Cl.
*A61F 13/02* (2006.01)
*A61M 1/00* (2006.01)
(Continued)

(52) U.S. Cl.
CPC .. *A61F 13/00068* (2013.01); *A61F 13/00991* (2013.01); *A61F 13/0216* (2013.01);
(Continued)

(58) Field of Classification Search
CPC ................ A61F 13/00; A61F 13/00068; A61F 13/00991; A61F 13/0216; A61F 13/0276;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Keri J Nelson

(57) ABSTRACT

A reduced-pressure treatment system for treating a wound on a patient includes a composite manifold that may help prevent or minimize injury to a wound edge of the wound being treated with reduced pressure. The composite manifold includes a perimeter manifold member and an inboard manifold member. The perimeter manifold member is designed to not collapse substantially under reduced pressure in a therapy range. The perimeter manifold member may be more rigid with respect to compressibility than the inboard manifold member. A sealing member is used to form a fluid seal over the wound, and a reduced-pressure subsystem provides reduced pressure to the composite manifold. Other systems, methods, and dressings are presented.

31 Claims, 3 Drawing Sheets

Related U.S. Application Data

(60) Provisional application No. 61/115,763, filed on Nov. 18, 2008.

(51) Int. Cl.
*A61F 13/00* (2006.01)
*A61M 27/00* (2006.01)

(52) U.S. Cl.
CPC ... *A61M 1/0088* (2013.01); *A61F 2013/0028* (2013.01); *A61F 2013/00314* (2013.01); *A61M 1/0023* (2013.01); *A61M 27/00* (2013.01); *A61M 2207/00* (2013.01); *Y10T 29/49885* (2015.01)

(58) Field of Classification Search
CPC ... A61M 1/0023; A61M 1/0088; A61M 27/00
USPC ....... 602/41–43, 46, 53; 604/289, 304, 305, 604/307, 308, 313
See application file for complete search history.

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 6,942,650 B1* | 9/2005 | Schultz ............... B01D 46/24 454/66 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0079852 A1 | 4/2006 | Bubb et al. |
| 2007/0027414 A1* | 2/2007 | Hoffman ............... A61F 13/02 602/2 |
| 2008/0015480 A1* | 1/2008 | Benz ............... A61K 36/886 602/42 |

FOREIGN PATENT DOCUMENTS

| | | |
|---|---|---|
| AU | 755496 | 2/2002 |
| CA | 2005436 | 6/1990 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 3/1999 |
| WO | 80/02182 A1 | 10/1980 |

(56) References Cited

FOREIGN PATENT DOCUMENTS

| WO | 87/04626 A1 | 8/1987 |
|---|---|---|
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/the British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for Pot International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đukić, Ž. Maksimović, Đ . Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

* cited by examiner

ND-PRESSURE, COMPOSITE MANIFOLDS

RELATED APPLICATION

This application is a continuation of U.S. patent application Ser. No. 12/620,086, entitled "A Reduced-Pressure, Composite Manifolds," filed 17 Nov. 2009, which claims the benefit, under 35 U.S.C. §119(e), of the filing of U.S. Provisional Patent Application Ser. No. 61/115,763, entitled "A Reduced-Pressure, Composite Manifold," filed 18 Nov. 2008, each of which is incorporated herein by reference for all purposes.

BACKGROUND

The present invention relates generally to medical treatment systems and, more particularly, to reduced-pressure, composite manifolds, methods, and systems.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue.

In the course of reduced-pressure treatment, issues with necrotic tissue or other issues at the wound margins may occur. These issues may occur even when the healthcare provider debrides the wound at each wound dressing change.

SUMMARY

Problems with existing reduced-pressure systems and methods are addressed by the dressings, systems and methods of the illustrative embodiments described herein.

According to an illustrative, non-limiting embodiment, a reduced-pressure treatment system for treating a wound on a patient, includes a composite manifold, a sealing member for coupling to the patient's epidermis and operable to form a fluid seal over the wound, and a reduced-pressure subsystem for providing reduced pressure to the composite manifold. The composite manifold includes a perimeter manifold member for disposing adjacent to a wound edge and having an interior portion, and an inboard manifold member disposed adjacent to the interior portion of the perimeter manifold member. The perimeter manifold member is formed with adequate strength to resist collapse under a compressive force transmitted by the sealing member when under therapeutic reduced pressure.

According to another illustrative, non-limiting embodiment, a composite manifold for use in a reduced-pressure treatment system includes a perimeter manifold member for disposing adjacent to a wound edge and having an interior portion, and an inboard manifold member disposed adjacent to the interior portion of the perimeter manifold member. The perimeter manifold member is formed with adequate strength to resist collapse under therapeutic reduced pressure.

According to another illustrative, non-limiting embodiment, a method of manufacturing a composite manifold for use in a reduced-pressure treatment system includes the steps of: forming a perimeter manifold member for disposing adjacent to a wound edge; forming an inboard manifold member; disposing the perimeter manifold member adjacent an interior portion of the perimeter manifold member. The perimeter manifold member is formed with adequate strength to resist collapse under therapeutic reduced pressure.

According to another illustrative, non-limiting embodiment, a method of treating a wound site on a patient with reduced pressure includes the steps of: disposing a composite manifold adjacent to the wound site; forming a fluid seal over the composite manifold; and fluidly coupling a reduced-pressure source to the composite manifold. The composite manifold includes a perimeter manifold member for disposing adjacent to a wound edge and having an interior portion, and an inboard manifold member disposed adjacent to the interior portion of the perimeter manifold member. The perimeter manifold member is formed with adequate strength to resist collapse under therapeutic reduced pressure.

According to another illustrative, non-limiting embodiment, a composite manifold for use in a reduced-pressure treatment system includes a perimeter manifold member for disposing proximate a wound edge, an inboard manifold member disposed adjacent to the perimeter manifold member, and wherein the perimeter manifold member is more rigid with respect to compressibility than the inboard manifold member.

Other objects, features, and advantages of the illustrative embodiments will become apparent with reference to the drawings and detailed description that follow.

BRIEF DESCRIPTION OF THE DRAWINGS

A more complete understanding of the present invention may be obtained by reference to the following Detailed Description when taken in conjunction with the accompanying Drawings wherein.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1A:
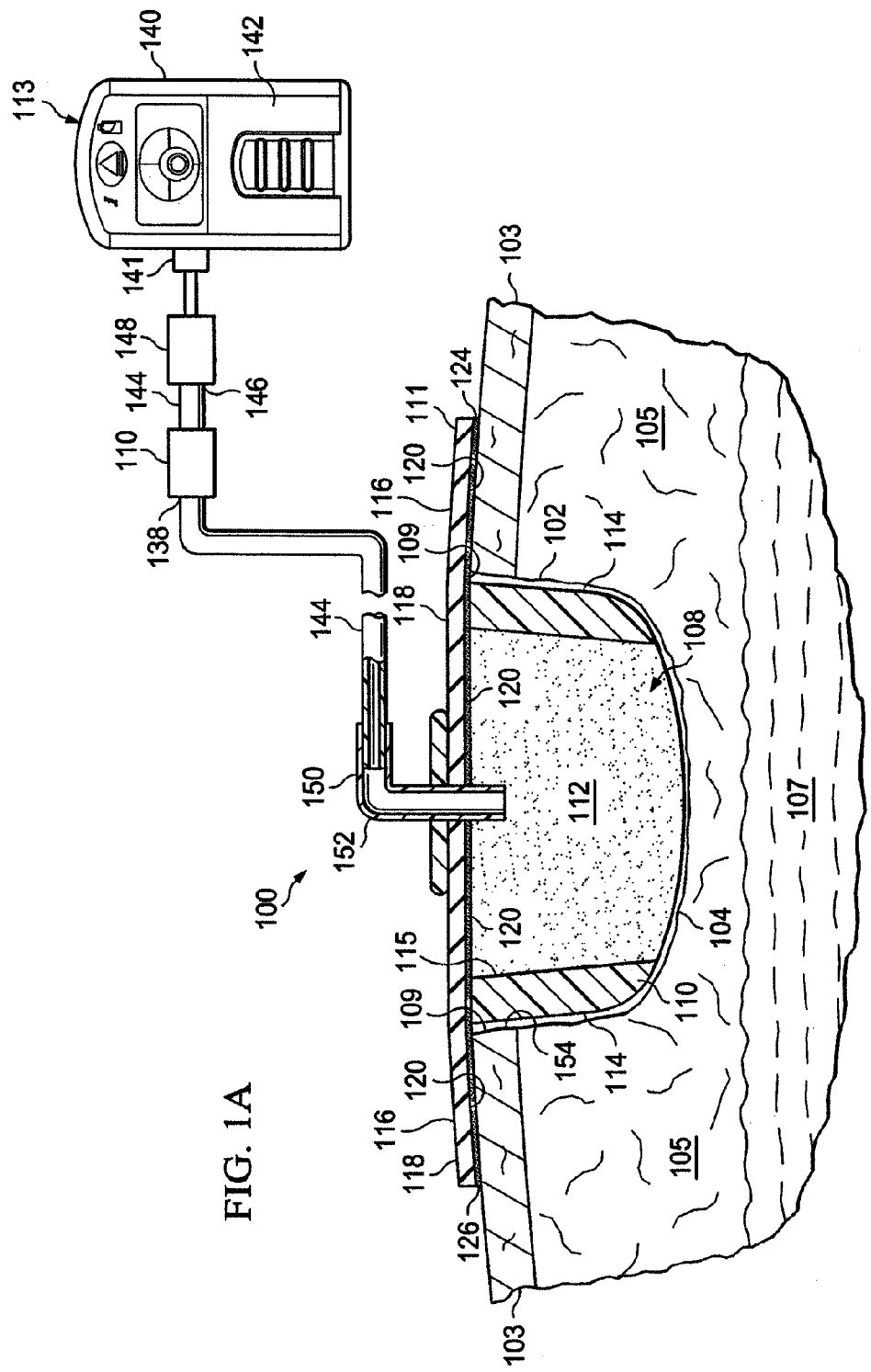
FIG. 1A is a schematic diagram with a portion shown in cross section of an illustrative embodiment of a reduced-pressure treatment system employing an illustrative composite manifold shown without reduced pressure applied.
Figure 1B:
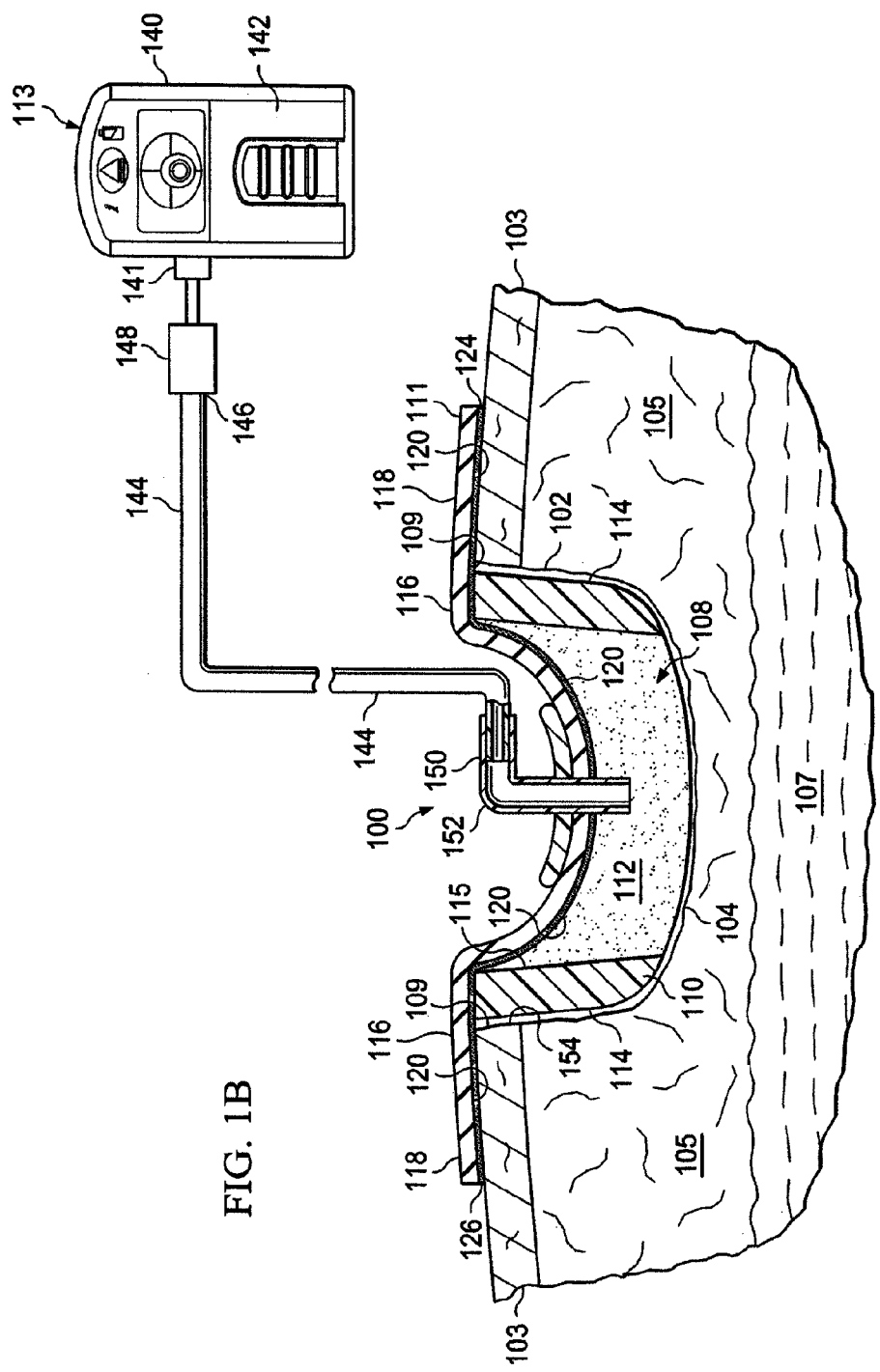
FIG. 1B is a schematic diagram with a portion shown in cross section of the illustrative embodiment of a reduced-pressure treatment system of FIG. 1 shown with reduced pressure applied.

Referring now primarily to FIGS. 1A and 1B, an illustrative, non-limiting embodiment of a reduced-pressure treatment system 100 for treating a wound 102 at a tissue site 104, which is centered in a wound bed, is presented. The wound 102 may be through or involve epidermis 103, dermis 105, and subcutaneous tissue 107. The reduced-pressure treatment system 100 may also be used at other tissue sites. The tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. Unless otherwise indicated, as used herein, "or" does not require mutual exclusivity.

The reduced-pressure treatment system 100 includes a composite manifold 108. In addition, the reduced-pressure treatment system 100 may include the sealing member 111 and a reduced-pressure subsystem 113. The composite manifold 108 includes a perimeter manifold member 110 and an inboard manifold member 112.

In one illustrative embodiment, the perimeter manifold member 110 and inboard manifold member 112 are made from a porous and permeable foam or foam-like material and, more particularly, a reticulated, open-cell polyurethane or polyether foam that allows good permeability of wound fluids while under a reduced pressure. One such foam material that has been used is the V.A.C.® GranuFoam® Dressing available from Kinetic Concepts, Inc. (KCI) of San Antonio, Tex. Any material or combination of materials may be used for the manifold material provided that the manifold material is operable to distribute the reduced pressure. The term "manifold" as used herein generally refers to a substance or structure that is provided to assist in applying reduced pressure to, delivering fluids to, or removing fluids from a tissue site. A manifold typically includes a plurality of flow channels or pathways. The plurality of flow channels may be interconnected to improve distribution of fluids provided to and removed from the area of tissue around the manifold. Examples of manifolds may include, without limitation, devices that have structural elements arranged to form flow channels, cellular foam, such as open-cell foam, porous tissue collections, and liquids, gels, and foams that include or cure to include flow channels. The manifold material may also be a combination or layering of materials; for example, a first manifold layer of hydrophilic foam may be disposed adjacent to a second manifold layer of hydrophobic foam to form the composite manifold 108.

The reticulated pores of the GranuFoam® material, that are in the range of about 400 to 600 microns, are helpful in carrying out the manifold function, but again other materials may be used. A material with a higher, or lower, density (smaller pore size) than GranuFoam® material may be desirable in some situations. Among the many possible materials, the following may be used: GranuFoam® material or a Foamex® technical foam (www.foamex.com). In some instances it may be desirable to add ionic silver to the foam in a microbonding process or to add other substances to the material, such as antimicrobial agents. The composite manifold 108 could be a bio-absorbable material or an anisotropic material.

The composite manifold 108 helps to address a situation involving wound edge 109, or tissue edge. Pressure patterns on the tissue at the wound edge 109 can increase tissue morbidity. Often as reduced pressure increases within a manifold, a force is applied on the wound edge 109. This pressure at the wound edge 109 may reduce perfusion at the wound margins.

The perimeter manifold 110 can provide support for the wound edge 109. In one aspect, the perimeter manifold 110 results in a composite manifold 108 that reduces pinching or prolapsing of the wound edge 109. The perimeter manifold member 110 may be formed from a manifold material that is more rigid, i.e., compresses less under pressure, than the inboard manifold member 112. The perimeter manifold member 110 carries a force that otherwise would be supported by the wound margin, or wound edge 109, if not borne by the perimeter manifold member 110. Thus, the use of the perimeter manifold 110 can reduce the amount of pressure that would otherwise be applied at the wound edge 109. The perimeter manifold member 110 helps keep the sealing member 111 from pulling in on the wound edge 109 in a direct fashion when under reduced pressure. In other words, the perimeter manifold member 110 helps transfer the inward force created by the sealing member 111 onto the composite manifold 108 and lowers the force on the wound edge 109. This transfer is believed to help increase perfusion at the wound edge 109.

The perimeter manifold member 110 is designed not to collapse substantially under reduced pressure in a therapy range and typically is more rigid than the inboard manifold member 112. The rigidity of perimeter manifold member 110 as compared to the inboard manifold member 112 may be accomplished in a number of ways and described in a number of ways.

One may consider the bulk modulus (K) of the perimeter manifold member 110 and the inboard manifold member 112. The bulk modulus (K) of a substance generally measures the substance's resistance to uniform compression. The bulk modulus is often defined as the pressure increase needed to effect a given relative decrease in volume. The bulk modulus K can be more formally defined by the equation: $K=\partial p/\partial V$, where p is pressure, V is volume, and $\partial p/\partial V$ denotes the partial derivative of pressure with respect to volume. Thus, in general terms, the more rigid a material is, the larger its bulk modulus. In the illustrative embodiment, the perimeter manifold member 110 may be formed from a first manifold material having a first bulk modulus $K_1$ and the inboard manifold member 112 may be formed from a second manifold material having a second bulk modulus $K_2$. Since in this embodiment the perimeter manifold member 110 is more rigid than the inboard manifold member 112, it follows that $K_1 > K_2$.

One may also consider the relative densities, ρ, of the perimeter manifold member 110 and inboard manifold member 112. The density (ρ) of a body is a measure of how tightly the matter within the body is packed together and is given by the ratio of its mass (m) to its volume (V). The composite manifold 108 may be formed with the perimeter manifold member 110 formed from a first manifold material having a first density, $\rho_1$, and the inboard manifold member 112 formed from a second manifold material having a second density, $\rho_2$, and where $\rho_1 > \rho_2$. With $\rho_1 > \rho_2$ the perimeter manifold 110 may have more rigidity than the inboard manifold 112. As one illustrative, non-limiting example, the inboard manifold member 112 could be formed from a GranuFoam® material having 65 pores per linear inch and the perimeter manifold member 110 could be formed from a GranuFoam® material having about 115 pores per linear inch.

Figure 4:
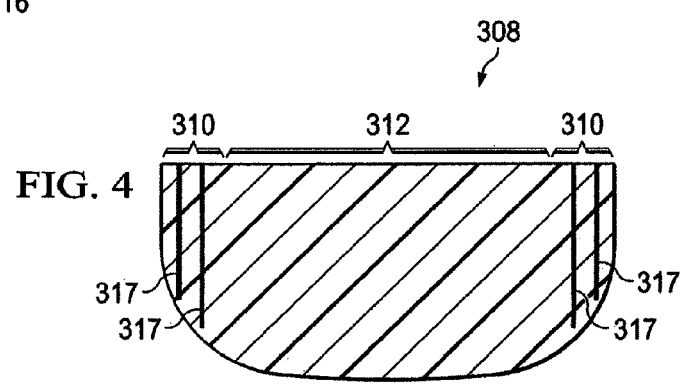
FIG. 4 is a schematic, cross-sectional view of an illustrative embodiment of another composite manifold.

In addition to forming the perimeter manifold member 110 and inboard manifold member 112 from the same material but with greater density (ρ) in the perimeter manifold member 110, the perimeter manifold member 110 and inboard manifold member 112 may be formed of different materials with the perimeter manifold member 110 selected to have more rigidity due to a higher density or a greater bulk modulus. In addition or as an alternative, as shown in FIG. 4, support elements 317 (e.g., filaments, vertical posts, struts, or other members) may be added into the first manifold material used as an aspect of forming the perimeter manifold member 310 to cause the perimeter manifold member 310 to be less compressible. With the addition of support elements 317, the perimeter manifold member 310 and the inboard manifold member 312 of the composite manifold 308 may be formed from the same manifold material, but the perimeter manifold member 310 will have more strength to resist collapse due to the support elements.

Alternatively or in addition, a manifold material may be sprayed with bio-friendly stiffening substance to cause a perimeter portion to be more stiff than an inboard portion while maintaining the ability for the perimeter portion to manifold fluids. In this manner, the perimeter manifold member 110 and inboard manifold member 112 may be formed. Any suitable bio-friendly stiffening substance may be used that allows the receiving manifold material to continue to manifold, or distribute, fluids; an example is a rapidly curing polyurethane spray. In still another illustrative embodiment, the perimeter manifold member 110 could be applied as a spray or gel directly against the wound edge 109 to form the perimeter manifold member 110 in situ and then a manifold member may be deployed in an interior portion that would form the inboard manifold member 112.

The perimeter manifold member 110 may be formed with an interior portion 115 and the inboard manifold member 112 may be disposed adjacent, which includes into, the interior portion 115. The perimeter manifold member 110 and the inboard manifold member 112 may be disposed adjacent to one another without more or may be coupled to one another by an adhesive, bonding, welding, or other means and thus formed as an integral unit. The perimeter manifold member 110 and the inboard manifold member 112 may also be separated by a space or by one or more items. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling.

Figure 2:
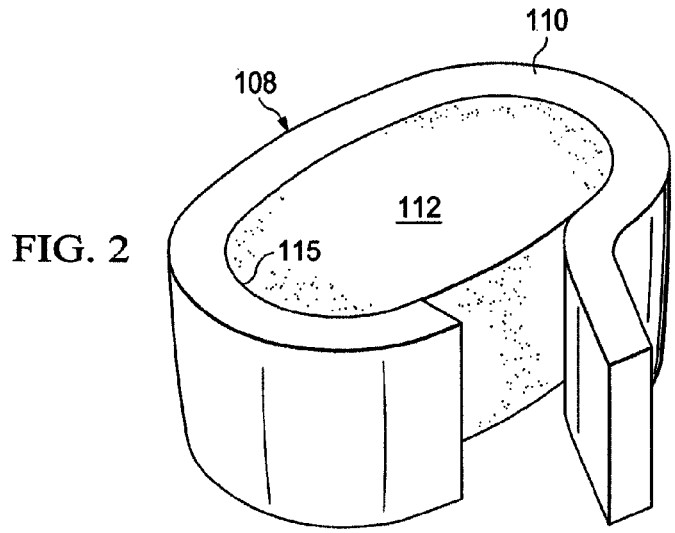
FIG. 2 is a schematic, perspective view of an illustrative embodiment of a composite manifold.

As shown in FIGS. 1A-1B, the composite manifold 108 may be formed with separate and distinct pieces placed adjacent to each other to form separate vertical regions that make up the perimeter manifold member 110 and the inboard manifold member 112. Moreover, as suggested in FIG. 2, the perimeter manifold member 110 may be a manifold strip, or tape, that is sized for the wound 102 and then placed in the wound against wound edge 109. At the same time, the inboard manifold member 112 may be appropriately sized and placed in the wound 102 to form the composite manifold 108. Similarly, if the perimeter manifold member 110 is embodied as a manifold strip, or tape, the inboard manifold member 112 may be approximately sized and configured to the size of the wound 102 and then the manifold strip, or tape, may be secured around a periphery of the inboard manifold member 112 to form the composite manifold 108. In one embodiment, the perimeter manifold member 110 itself may be an integral piece or may be formed from a plurality of manifold members.

Figure 3:
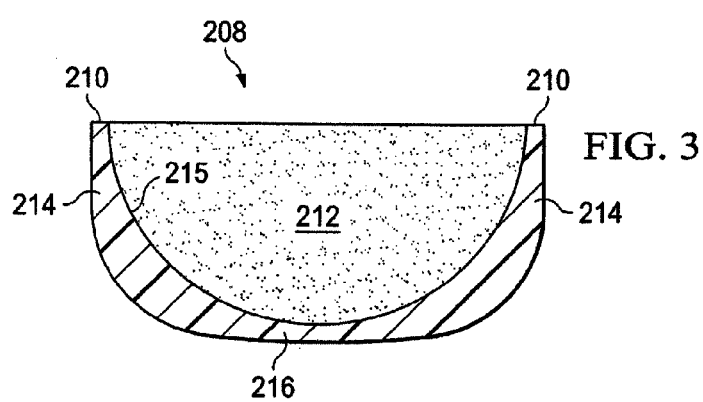
FIG. 3 is a schematic, cross-sectional view of an illustrative embodiment of another composite manifold.

There are many other ways to form the composite manifold 108. As another illustrative embodiment, FIG. 3 shows a composite manifold 208 having perimeter manifold member 210 that includes walls 214 and base 216 and that is made to cooperate with inboard manifold member 212. The base 216 may have apertures formed therein to further promote fluid flow through the base 216. The perimeter manifold member 210 may define an interior portion 215 into which the inboard manifold member 212 is disposed. The perimeter manifold member 210 and inboard manifold member 212 may be uncoupled, but nested, or may be coupled. Moreover, the perimeter manifold member 210 and inboard manifold member 212 may be formed as an integral unit with varying properties. As an alternative, the inboard manifold member 212 could be formed as a plurality of manifolding spheres, or beads, placed on top of the perimeter manifold member 210. Regardless of how made, the composite manifold 108 is formed so that the perimeter manifold member 210 prevents a compressive force from being applied to the wound edge, and in one embodiment, compresses—at least downwardly for the orientation shown—under reduced pressure less than the inboard manifold member 212.

A bioactive material may be added to the perimeter manifold members 110, 210 to help provide treatment and care to the wound edge (e.g., wound edge 109 in FIG. 1). Examples of a bioactive materials include epinephrine (or other dilating agents); vasoconstrictor or hemorrhage related material, such as thromboxane A2, prostaglandin 2a, prostaglandin 2-alpha, fibronectin, fibrinogen, von Willebrand factor; vasodilatation related material, such as histamine; chemokine related material, such as platelet derived growth factor, epidermal growth factor; cell growth related material, such as transforming growth factor, epidermal growth factor, insulin-like growth factor, keratinocyte growth factor; and analgesics, such as lidocaine, rubefacients, capsaicin, and NSAIDs; etc. A bioactive material may also be added to the inboard manifold member 112.

Referring again primarily to FIGS. 1A and 1B, the sealing member 111 covers the composite manifold 108 and extends past a peripheral edge 114 of the composite manifold 108 to form a sealing-member extension 116. The sealing-member extension 116 has a first side 118 and a second, patient-facing side 120. The sealing-member extension 116 may be sealed against epidermis 103 or against a gasket or drape by sealing apparatus 124, such as a pressure-sensitive adhesive 126. The sealing apparatus 124 may take numerous forms, such as an adhesive sealing tape, or drape tape or strip; double-side drape tape; pressure-sensitive adhesive 126; paste; hydrocolloid; hydrogel; or other sealing means. If a tape is used, the tape may be formed of the same material as the sealing member 111 with a pre-applied, pressure-sensitive adhesive. The pressure-sensitive adhesive 126 may be applied on a second, patient-facing side 120 of the sealing-member extension 116. The pressure-sensitive adhesive 126 provides a substantially fluid seal between the sealing member 111 and the epidermis 103, which, as used herein, is also deemed to include a gasket or drape against the epidermis 103. Before the sealing member 111 is secured to the epidermis, removable strips covering the pressure-sensitive adhesive 126 may be removed. As used herein, "fluid seal," or "seal," means a seal adequate to maintain reduced pressure at a desired site given the particular reduced-pressure source or subsystem involved.

The sealing member 111 may be an elastomeric material or any material or substance that provides a fluid seal. "Elastomeric" means having the properties of an elastomer and generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Further still, sealing member materials may include a silicone drape, 3M Tegaderm® drape, acrylic drape such as one available from Avery Dennison, or an incise drape.

The reduced-pressure subsystem 113 includes a reduced-pressure source 140, which can take many different forms. The reduced-pressure source 140 provides a reduced pressure as a part of the reduced-pressure treatment system 100. As used herein, "reduced pressure" generally refers to a pressure less than the ambient pressure at a tissue site 104 that is being subjected to treatment. In most cases, this reduced pressure will be less than the atmospheric pressure at which the patient is located. Alternatively, the reduced pressure may be less than a hydrostatic pressure at a tissue site. Reduced pressure may initially generate fluid flow in the manifold 112, delivery conduit 144, and adjacent to the tissue site 104. As the hydrostatic pressure around the tissue site 104 approaches the desired reduced pressure, the flow may subside, and the reduced pressure may be maintained. Unless otherwise indicated, values of pressure stated herein are gauge pressures.

The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

Referring to the illustrative embodiment of FIGS. 1A-1B, the reduced-pressure source 140 is shown having a reservoir region 142, or canister region. An interposed membrane filter, such as hydrophobic or oleophobic filter, may be interspersed between the delivery conduit, or tubing, 144 and the reduced-pressure source 140. A portion 146 of delivery conduit 144 may have one or more devices, such as a representative device 148. The device 148 may be, for example, another fluid reservoir, or collection member to hold exudates and other fluids removed, a pressure-feedback device, a volume detection system, a blood detection system, an infection detection system, a flow monitoring system, a temperature monitoring system, etc. Multiple devices 148 may be included. Some of these devices may be formed integral to the reduced-pressure source 140. For example, a reduced-pressure port 141 on reduced-pressure source 140 may include a filter member that includes one or more filters, e.g., an odor filter.

The reduced-pressure source 140 may be any device for supplying a reduced pressure, such as a vacuum pump, wall suction, or other source. While the amount and nature of reduced pressure applied to a tissue site will typically vary according to the application, the reduced pressure will typically be between −5 mm Hg and −500 mm Hg and more typically in a therapeutic range between −100 mm Hg and −200 mm Hg.

The reduced pressure developed by reduced-pressure source 140 is delivered through the delivery conduit 144 to a reduced-pressure interface 150, which may include an elbow port 152. In one illustrative embodiment, the elbow port 152 is a TRAC® technology port available from Kinetic Concepts, Inc. of San Antonio, Tex. The reduced-pressure interface 150 allows the reduced pressure to be delivered through the sealing member 111 to the composite manifold 108, as well as to a sealed space 154, in which the composite manifold 108 is located. In this illustrative embodiment, the reduced-pressure interface 150 extends through the sealing member 111 and into the composite manifold 108.

In operation according to one illustrative embodiment, the composite manifold 108 is placed adjacent the tissue site 104, e.g., in the wound bed on wound 102, with the perimeter manifold member 110 adjacent, or proximate, the wound edge 109. If a tape-style perimeter manifold member 110 is used as part of the composite manifold 108, the tape-style perimeter manifold member 110 would be uncoiled to track the wound perimeter or wound edge 109 of the wound 102 and then an appropriate size of the inboard manifold member 112 would be sized to go into a center portion defined by the perimeter manifold member 110. Alternatively, the inboard manifold member 112 may be sized to approximately match that of the wound 102 (allowing a small gap for the perimeter manifold member 110) and then tape placed on the periphery of the inboard manifold member 112 to form the composite manifold 108.

The sealing member 111 is then placed over the tissue site 104 and the composite manifold 108 and at least partially against epidermis 103 (or gasket or drape) to form a fluid seal and formed the sealed space 154. If not already installed, the reduced-pressure interface 150 is installed. The delivery conduit 144 is fluidly coupled to the reduced-pressure interface 150 and the reduced-pressure source 140 whereby reduced pressure may be provided to the composite manifold 108. The reduced-pressure source 140 may be activated to begin the delivery of reduced pressure to the composite manifold 108 in the sealed space 154.

When reduced pressure is supplied to the composite manifold 108, the composite manifold 108 compresses from an uncompressed state (FIG. 1A) to a compressed state (FIG. 1B). As seen in FIG. 1B, under reduced pressure, the more rigid perimeter manifold member 110 does not collapse and is available to carry any load that might otherwise be asserted by the sealing member 111 on to the wound edge 109 during reduced-pressure treatment of the wound 102 or tissue site 104. In the illustrative embodiment of FIG. 1B, the perimeter manifold member 110 does not compress as much as the inboard manifold member 112 and the less rigid inboard manifold member 112 may facilitate the patient's movement and comfort.

The system 100 allows reduced-pressure treatment to be applied with minimized compression at the wound margin, or wound edge, so as to minimize or prevent injury. The system 100 allows a bioactive factor to be readily applied to the wound edge 109.

While the illustrative embodiments present discrete portions (e.g., perimeter manifold member 110 and inboard manifold member 112) of the composite manifold 108, 208, it should be understood that the a gradual change may be used between portions or that a single piece of material may be used with support elements added. While the perimeter manifold member 110 is shown extending thickness of the inboard manifold member 112, in another embodiment, the perimeter manifold 110 may only be at a top portion (for the orientation of FIG. 1A) of the inboard manifold member 112.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

What is claimed is:

1. A system for providing reduced-pressure treatment to a wound, the system comprising:
    an inboard manifold having a first rigidity;
    a perimeter manifold circumscribing the inboard manifold, the perimeter manifold having a second rigidity that is greater than the first rigidity of the inboard manifold;
    a sealing member configured to be placed over the inboard manifold and the perimeter manifold to form a sealed space; and
    a reduced-pressure source configured to be fluidly coupled to the sealed space to provide a therapeutic reduced pressure;
    wherein the perimeter manifold has adequate strength to resist collapse under compressive force transmitted by the sealing member when under therapeutic reduced pressure.

2. The system of claim 1, wherein a bulk modulus of the perimeter manifold is greater than a bulk modulus of the inboard manifold.

3. The system of claim 1, wherein a density of the perimeter manifold is greater than a density of the inboard manifold.

4. The system of claim 1, further comprising support elements disposed in the perimeter manifold.

5. The system of claim 4, wherein the support elements comprise filaments.

6. The system of claim 4, wherein the support elements comprise vertical posts.

7. The system of claim 4, wherein the support elements comprise struts.

8. The system of claim 1, further comprising a bio-friendly stiffening substance coating the perimeter manifold.

9. The system of claim 8, wherein the bio-friendly stiffening substance comprises a gel configured to be applied to an edge of a wound, and the perimeter manifold is configured to be coated by the bio-friendly stiffening substance in situ.

10. The system of claim 1, wherein the perimeter manifold comprises a tape applied to the periphery of the inboard manifold.

11. The system of claim 1, wherein the perimeter manifold is configured to support a wound edge.

12. The system of claim 11, wherein the perimeter manifold is configured to carry a load asserted by the sealing member.

13. The system of claim 1, wherein the perimeter manifold is configured to carry a load asserted by the sealing member.

14. A manifold for use with a reduced-pressure treatment system, the manifold comprising:
    an inboard manifold having a first rigidity; and
    a perimeter manifold circumscribing the inboard manifold, the perimeter manifold having a second rigidity that is greater than the first rigidity of the inboard manifold;
    wherein the perimeter manifold has adequate strength to resist collapse under compressive force transmitted by a sealing member when under therapeutic reduced pressure.

15. The manifold of claim 14, wherein a bulk modulus of the perimeter manifold is greater than a bulk modulus of the inboard manifold.

16. The manifold of claim 14, wherein a density of the perimeter manifold is greater than a density of the inboard manifold.

17. The manifold of claim 14, further comprising support elements disposed in the perimeter manifold.

18. The manifold of claim 17, wherein the support elements comprise filaments.

19. The manifold of claim 17, wherein the support elements comprise vertical posts.

20. The manifold of claim 17, wherein the support elements comprise struts.

21. The manifold of claim 14, further comprising a bio-friendly stiffening substance coating the perimeter manifold.

22. The manifold of claim 21, wherein the bio-friendly stiffening substance comprises a gel configured to be applied to an edge of a wound, and the perimeter manifold is configured to be coated by the bio-friendly stiffening substance in situ.

23. The manifold of claim 14, wherein the perimeter manifold comprises a tape applied to the periphery of the inboard manifold.

24. The manifold of claim 14, wherein the perimeter manifold is configured to support a wound edge.

25. The manifold of claim 24, wherein the perimeter manifold is configured to carry a load asserted by the sealing member.

26. The manifold of claim 14, wherein the perimeter manifold is configured to carry a load asserted by the sealing member.

27. A method of manufacturing a composite manifold for use in a reduced-pressure treatment system, the method comprising the steps of:
    forming a perimeter manifold member adapted to support an edge of a wound and carry a load asserted by a sealing member when under therapeutic reduced pressure, the perimeter manifold member having an interior portion and a first bulk modulus K1;
    forming an inboard manifold member having a second bulk modulus K2, wherein K1 is greater than K2; and
    disposing the inboard manifold member adjacent the interior portion of the perimeter manifold member.

28. The method of claim 27, further comprising the step of coupling the perimeter manifold member to the inboard manifold member.

29. The method of claim 27, wherein the steps of forming a perimeter manifold member and forming an inboard manifold member comprise the steps of:
    forming the perimeter manifold member from a first manifold material having a first density, $\rho_1$;

forming the inboard manifold member from a second manifold material having a second density, $\rho_2$; and wherein the first density is greater than the second density, $\rho_1 > \rho_2$.

30. The method of claim 27, wherein the step of forming a perimeter manifold member comprises the steps of forming the perimeter manifold member from a first manifold material and applying a bioactive material to at least a portion of the first manifold material.

31. The method of claim 27, wherein the step of forming a perimeter manifold member comprises the steps of forming the perimeter manifold member from a first manifold material and applying a bioactive material to at least a portion of the first manifold material and wherein the bioactive material comprises epinephrine.

* * * * *